April. 1, 1969 F. W. ANDERSON Plant Pat. 2,878
NECTARINE TREE
Filed Sept. 27, 1967
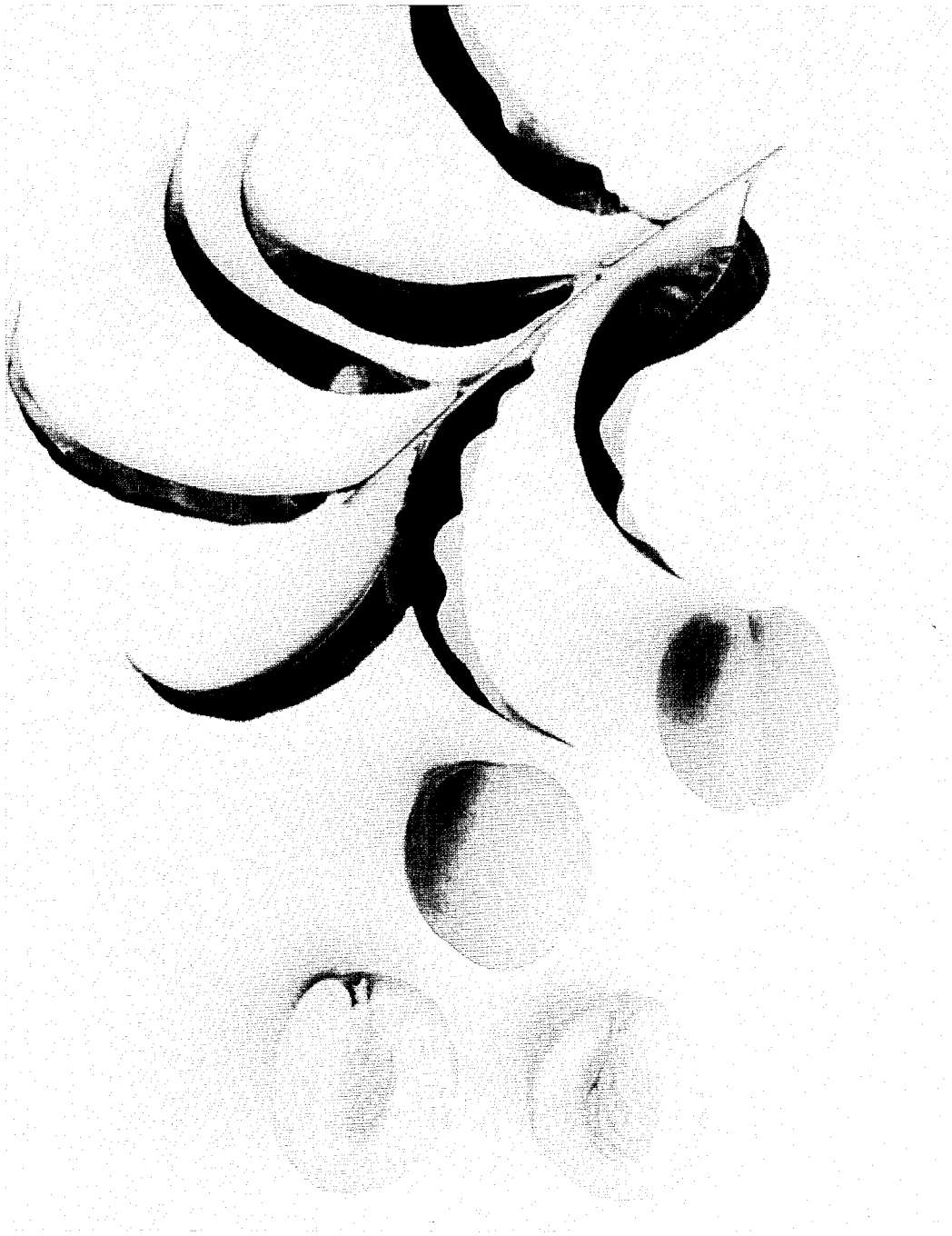
INVENTOR
Frederic W. Anderson
BY Webster & Webster
ATTORNEYS

United States Patent Office

Plant Pat. 2,878
Patented Apr. 1, 1969

2,878

NECTARINE TREE

Frederic W. Anderson, Merced, Calif., assignor to Reedley Nursery, Inc., Reedley, Calif., a corporation of California

Filed Sept. 27, 1967, Ser. No. 671,169
Int. Cl. A01h *5/08*
U.S. Cl. Plt.—41 1 Claim

ABSTRACT OF THE DISCLOSURE

A variety of nectarine tree which is a regular and productive bearer of large freestone fruit having yellow flesh, and yellow skin substantially entirely overspread with red at shipping maturity; the variety being embraced by Group III (with sweet kernels) of the classification established by Caillavet and Souty in their Monographie des Principales Variétés de Pêchers, 1950 edition.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety*

The present variety of nectarine tree was originated by me, at my experimental nursery and orchard located as aforesaid, as a cross between Red Grand nectarine (United States Plant Patent No. 1,060) and an unnamed seedling of Early Sun Grand nectarine (United States Plant Patent No. 1,420). One seedling from such cross evidenced desirable characteristics and was, therefore, selected by me for asexual reproduction.

*Asexual reproduction of the variety*

Subsequent to origination of the variety, as above, I asexually reproduced it by top-working on mature trees in my aforementioned orchard. In maturity, all of such reproductions ran true to the original tree in all respects.

*Summary of the variety*

The present variety is characterized by a large, vigorous tree which is a regular and productive bearer of large, slightly elongated, freestone fruit having yellow flesh, and yellow skin substantially entirely overspread with red at shipping maturity; the variety—while generally similar to the Early Sun Grand—being distinctive in that the fruit ripens immediately thereafter but with the harvest usually complete before the start of harvest of the Star Grand II (United States Plant Patent No. 1,646).

*Brief description of the drawing*

The drawing is an illustration, by photographic reproduction in color, of fruit of the variety, together with a twig with leaves; the view including one fruit cut in half in the suture plane, with the stone remaining in one half.

*Description of the variety*

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Color.*—Gray to green.
- *Lenticels.*—Number—medium.

Leaves:
- *Size.*—Large to medium. Average length—5". Average width—1¼".
- *Form.*—Lanceolate; acutely pointed.
- *Margin.*—Crenate.
- *Petiole.*—Medium length.
- *Glands.*—Number and position—usually 2 on petiole, and 1 to 3 on blade. Medium size; reniform.
- *Color.*—Top side—Medium Green (23–L–7). Under side—Lighter Green (22–L–5).

Flower buds: Length—medium.

Flowers:
- *Blooming period.*—Date of first bloom—Mar. 6, 1967. Date of full bloom—Mar. 22, 1967. Medium, as compared with other varieties.
- *Size.*—Large.
- *Color.*—Pink—showy.

Fruit:
- *Maturity when described.*—Hard ripe.
- *Date of first picking.*—July 14, 1967.
- *Date of last picking.*—July 22, 1967.
- *Size.*—Uniform; large. Average diameter axially—2⅞". Average transversely in suture plane—2⅛".
- *Form.*—Uniform; symmetrical; globose to oblong.
- *Suture.*—Distinct; extends from base to beyond apex; almost about entire circumference, with marked depression beyond pistil point.
- *Ventral surface.*—Lipped toward both sides.
- *Lips.*—Equal to unequal.
- *Cavity.*—Elongated in suture plane, with suture showing on one side; medium depth.
- *Apex.*—Short; depressed.
- *Pistil point.*—Minute.

Skin:
- *Thickness.*—Thick to medium.
- *Texture.*—Tough.
- *Tendency to crack.*—None noted.
- *Down.*—Wanting.
- *Color.*—Yellow (11–L–6) substantially overspread with red (4–L–6) to (6–L–6) at shipping maturity.

Flesh:
- *Juice.*—Moderate.
- *Texture.*—Firm; crisp; meaty.
- *Fibers.*—Few; fine.

*Ripens.*—Evenly.
*Flavor.*—Subacid.
*Aroma.*—Distinct to wanting.
*Eating quality.*—Good to best.
*Color.*—Yellow (10–L–4).

Stone:
*Type.*—Free.
*Size.*—Large to medium. Average length—1¼". Average breadth—1". Average thickness—¾".
*Form.*—Oblong to oval.
*Sides.*—Equal.
*Ridges.*—Rounded.
*Kernel.*—Sweet.
*Color.*—Desert Tan (12–J–7).

Use: Market; dessert.
Keeping quality: Good.
Shipping quality: Good.

The nectarine tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of nectarine tree, substantially as illustrated and described, which is a regular and productive bearer of large, slightly elongated, freestone fruit having yellow flesh, and yellow skin substantially entirely overspread with red at shipping maturity; the variety having general resemblance to the Early Sun Grand nectarine but being distinctively characterized in comparison by ripening immediately after said Early Sun Grand, and with the harvest usually complete before the start of harvest of the Star Grand II.

No references cited.

ROBERT E. BAGWILL, *Primary Examiner.*